United States Patent
Hao et al.

(10) Patent No.: US 9,637,502 B2
(45) Date of Patent: May 2, 2017

(54) CRYSTAL FORM OF CEFATHIAMIDINE COMPOUND AND PREPARATION METHOD THEREFOR

(71) Applicants: TIANJIN UNIVERSITY, Tianjin (CN); HAINAN LINGKANG PHARMACEUTICAL CO., LTD, Haikou (CN)

(72) Inventors: Hongxun Hao, Tianjin (CN); Linggang Tao, Haikou (CN); Zhihong Sun, Tianjin (CN); Baohong Hou, Tianjin (CN); Jun Lv, Haikou (CN); Qiuxiang Yin, Tianjin (CN); Yongli Wang, Tianjin (CN); Junbo Gong, Tianjin (CN); Chuang Xie, Tianjin (CN); Ying Bao, Tianjin (CN)

(73) Assignees: TIANJIN UNIVERSITY, Tianjin (CN); HAINAN LINGKANG PHARMACEUTICAL CO., LTD, Haikou (CN)

( * ) Notice: Subject to any disclaimer, the term of this patent is extended or adjusted under 35 U.S.C. 154(b) by 0 days.

(21) Appl. No.: 15/304,824

(22) PCT Filed: Nov. 20, 2015

(86) PCT No.: PCT/CN2015/095233
§ 371 (c)(1),
(2) Date: Oct. 17, 2016

(87) PCT Pub. No.: WO2016/107331
PCT Pub. Date: Jul. 7, 2016

(65) Prior Publication Data
US 2017/0044184 A1    Feb. 16, 2017

(30) Foreign Application Priority Data

Dec. 31, 2014 (CN) .......................... 2014 1 0853349

(51) Int. Cl.
C07D 501/28 (2006.01)
C07D 501/60 (2006.01)
C07D 501/12 (2006.01)

(52) U.S. Cl.
CPC ......... *C07D 501/60* (2013.01); *C07D 501/12* (2013.01); *C07D 501/28* (2013.01); *C07B 2200/13* (2013.01)

(58) Field of Classification Search
None
See application file for complete search history.

(56) References Cited

FOREIGN PATENT DOCUMENTS

CN          1462751 A   * 12/2003  ........... C07D 501/28

* cited by examiner

*Primary Examiner* — Golam M M Shameem
*Assistant Examiner* — Laura Daniel
(74) *Attorney, Agent, or Firm* — CBM Patent Consulting, LLC

(57) ABSTRACT

A novel crystalline form of Cefathiamidine compound and its preparation method, characterizing in its X-ray powder diffraction pattern and differential scanning calorimetry thermogram. Dissolving Cefathiamidine compound with a purity of 98% or higher in a solvent at a temperature of 30~45° C. to form a solution, whose concentration is controlled within 0.05~0.2 g/mL, and then adding a solventing-out agent to the solution, wherein the amount of the solventing-out agent is 3~5 times (in volume) of that of the solvent; followed by cooling the solution down to 0~10° C. at a rate of 0.2~1° C./min; continuing to stir for 1~3 hours, and separating the obtained solid-liquid suspension to provide a novel crystalline form of Cefathiamidine compound after drying.

7 Claims, 4 Drawing Sheets

CRYSTAL FORM OF CEFATHIAMIDINE COMPOUND AND PREPARATION METHOD THEREFOR

This application is the U.S. national phase of International Application No. PCT/CN2015/095233 Filed on 20 Nov. 2015 which designated the U.S. and claims priority to Chinese Application Nos. CN201410853349.X filed on 31 Dec. 2014, the entire contents of each of which are hereby incorporated by reference.

FIELD OF THE INVENTION

The invention relates to crystallization technology in chemical engineering field, in particular, to a novel crystalline form of Cefathiamidine compound and its preparation method by crystallization.

PRIOR ART

Cefathiamidine is also named as Cephalosporin 18, having a chemical name of (6R,7R)-3[(acetyloxy)methyl]-7-[α-(N,N'-diisopropyl-carbamimidoylsulfanyl)-acetylamino]-8-oxo-5-thia-1-aza-bicyclo[4,2,0]oct-2-ene-2-carboxylic acid ammonium salt, and a formula of $C_{19}H_{28}N_4O_6S_2$. It has a molar weight of 472.59 and the following chemical structure:

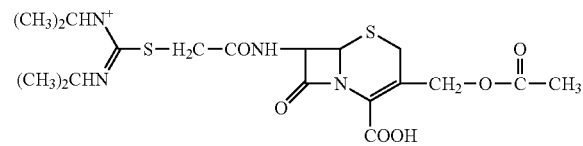

Cefathiamidine is a β-lactam antibiotic, belonging to the first-generation cephalosporins, which has a similar antibacterial spectrum with Cefalotin and shows antimicrobial activities against gram-positive bacterias and some gram-negative bacterias, therefore mainly is used for the treatment of respiratory tract infection, biliary tract infection, urinary tract infection, gynecological infections, sepsis, pneumonia, meningitis and so on, which are induced by *S. aureus* bacteria, pneumococcal and *streptococcus*.

Cefathiamidine is polymorphic, and various crystalline forms and their preparation methods have been reported by literatures. CN1462751A discloses a crystallized Cefathiamidine, its preparation method and use. The X-ray powder diffraction pattern of Cefathiamidine obtained by this method is shown in FIG. 1. In this method, the pH of a Cefathiamidine solution is adjusted within 3.5~6.5, the saturation process and the rate of crystal growth are controlled by adding proper solventing-out agent(s), and crystallized Cefathiamidine is obtained after crystallizing, filtering and drying. However, Cefathiamidine has a molecular structure of zwitterionic salt, which is unstable when heated and easy to form amorphous powder, leading to its low purity and poor storage stability. CN1495187A discloses a crystallized Cefathiamidine and its preparation method. The X-ray powder diffraction pattern of Cefathiamidine obtained by this method is shown in FIG. 2. In this method, crystallized Cefathiamidine is obtained by adding proper solventing-out agent(s) to a Cefathiamidine solution until crystallizing, thereafter separating and drying. This crystalline form, with a decomposition temperature of 154±1° C. or above, is more stable than amorphous form, but has a low crystallinity according to its XRD data. "Preparation and stability studies for different crystalline forms of Cefathiamidine" (Liu Shuyu, Sun Yuejiao, Preparation and stability studies for different crystalline forms of Cefathiamidine [J], Chinese Journal of Antibiotics, 2010, 35(10): 760-762) relates to researches on crystallization of Cefathiamidine in different solvents, and a novel crystalline form of Cefathiamidine is obtained from the solvent of acetonitrile. The X-ray powder diffraction pattern of this crystalline form of Cefathiamidine is shown in FIG. 3. However, the thermal cracking temperature (145.4° C.) of this crystalline form is lower than the thermal cracking temperature (153.2° C.) of the crystalline form II obtained by recrystallization from isopropanol, thus it has a poorer stability than that of the crystalline form prepared in CN1495187A. CN103012434A discloses a crystallized Cefathiamidine, its preparation method and pharmaceutical composition. The X-ray powder diffraction pattern of Cefathiamidine obtained by this method is shown in FIG. 4. This method has high operating temperature, large energy consumption and long process flow, and it may lead to liver damage with increased dosage due to sodium benzoate contained in the pharmaceutical composition.

In order to further improve the thermal stability and purity of Cefathiamidine compound, the present invention discloses a novel crystalline form of Cefathiamidine compound with higher melting point (169.6±1° C.) and higher thermal cracking temperature (172.2±1° C.), both higher than those of any reported crystalline forms. It has been found that this crystalline product shows good thermal stability in drug storage test. At the meantime, this crystalline product could arrive at a purity of 99.0% or above and a crystallization process yield of 85% or higher.

DETAILED DESCRIPTION OF THE INVENTION

The aim of the present invention is to provide a novel crystalline form of Cefathiamidine compound and its preparation method by crystallization.

The novel crystalline form of Cefathiamidine compound provided in the present invention is determined by X-ray powder diffraction, and the X-ray powder diffraction pattern comprises characteristic diffraction peaks (expressed in degrees 2θ) at 7.26°±0.2°, 8.08°±0.2°, 10.38°±0.2°, 12.64°±0.2°, 13.96°±0.2°, 14.52°±0.2°, 16.60°±0.2°, 19.22°±0.2°, 20.04°±0.2°, 21.14°±0.2°, 21.84°±0.2°, and 22.74°±0.2° as shown in FIG. 5.

The novel crystalline form of Cefathiamidine compound provided in the present invention is determined by differential scanning calorimeter, and the differential scanning calorimetry thermogram comprises a melting endothermic peak at 169.6±1° C. and a decomposing exothermic peak at 172.2±1° C. as shown in FIG. 6. Test conditions are as follows: temperature range, 25~200° C., temperature rising rate, 10° C./min, nitrogen protection: 80 mL/min.

A method for preparing the novel crystalline form of Cefathiamidine compound provided in the present invention is as follows:

Dissolving Cefathiamidine compound with a purity of 98% or higher in a solvent at a temperature of 30~45° C. to form a solution, whose concentration is controlled within 0.05~0.2 g/mL, and then adding a solventing-out agent to the solution, wherein the amount of the solventing-out agent is 3~5 times (in volume) of that of the solvent; followed by cooling the solution down to 0~10° C. at a rate of 0.2~1° C./min; continuing to stir for 1~3 hours, and separating the obtained solid-liquid suspension to provide a novel crystalline form of Cefathiamidine compound after drying.

In the above method, said solvent is selected from one of methanol, ethanol and water or a mixture thereof.

In the above method, said solventing-out agent is selected from one of n-propanol, isopropanol, n-butanol, cyclohexane and n-hexane or a mixture thereof.

In the above method, said solventing-out agent is dropwise added within 3~6 hours.

In the above method, said drying condition includes: t a temperature of 25~35° C., a vacuum of 0.08~0.1 MPa and a drying time of 4~8 hours.

The method for preparing a novel crystalline form of Cefathiamidine compound provided in the present invention is advantageous in its simple and easy-controlled operating conditions; easy-filtered, easy-washed and easy-dried crystal slurry of the product. X-ray powder diffraction result shows that the product has an integral crystalline form with high crystallinity, a one-way crystallization process mole yield of 85% or higher, and a purity of 99% or above. At the meantime, the novel crystalline product has a melting temperature of 169.6±1° C. and a thermal cracking temperature of 172.2±1° C., which are higher than those of any reported crystalline forms. It has also been found that the novel crystalline product possesses better thermal stability in stability studies.

It is shown on toxicity studies and in vitro antibacterial activity tests that the novel crystalline form of Cefathiamidine compound provided in the present invention is better than any prior art and more suitable for clinical research and application.

EMBODIMENTS OF THE INVENTION

The present invention is further illustrated by the following figures and examples. By these illustration, features and advantages of the present invention becomes more clear and more definite.

Example 1

Figure 1:
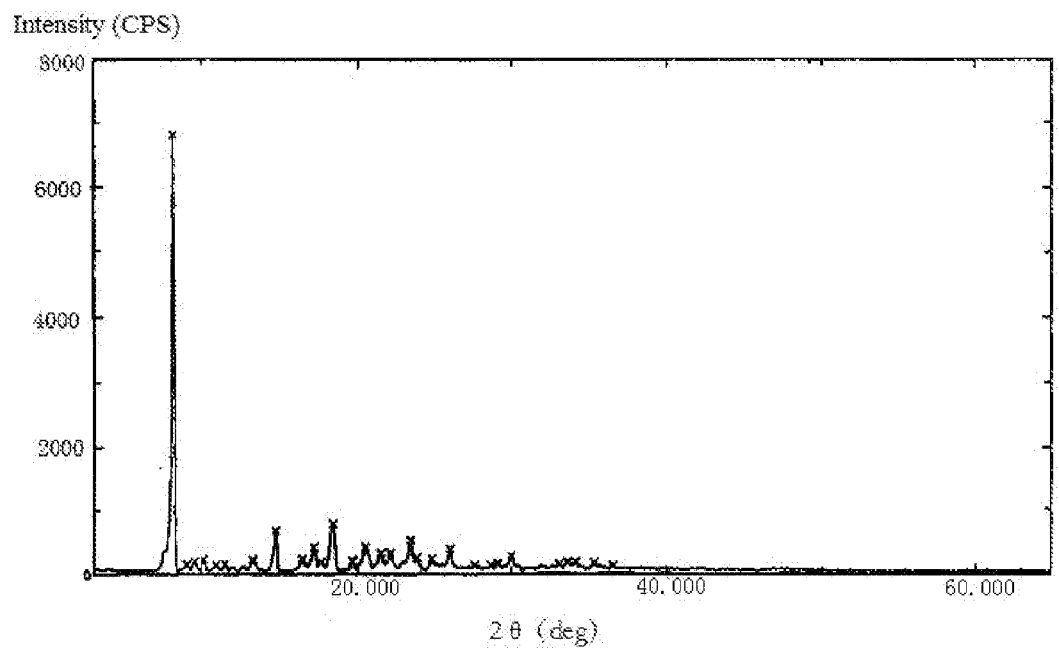
FIG. 1 provides the X-ray powder diffraction pattern of crystallized Cefathiamidine disclosed in CN1462751A.
Figure 2:
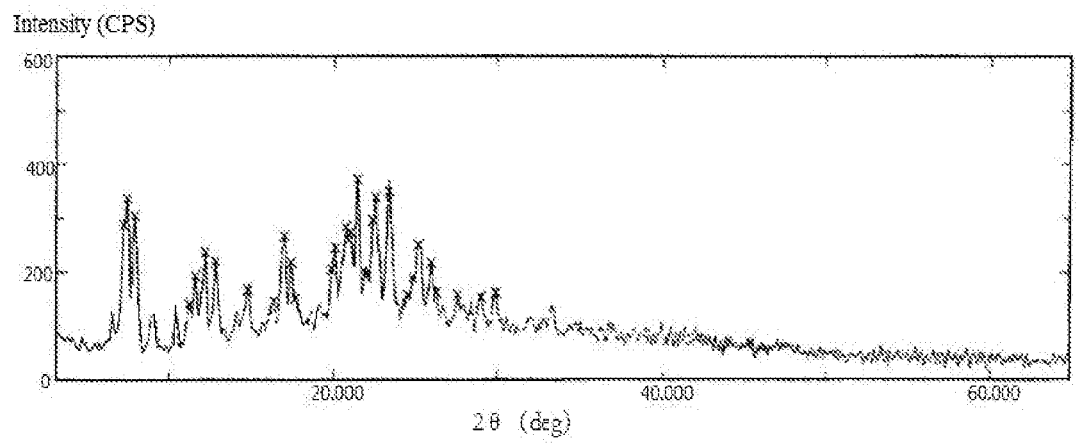
FIG. 2 provides the X-ray powder diffraction pattern of crystallized Cefathiamidine disclosed in CN1495187A.
Figure 3:
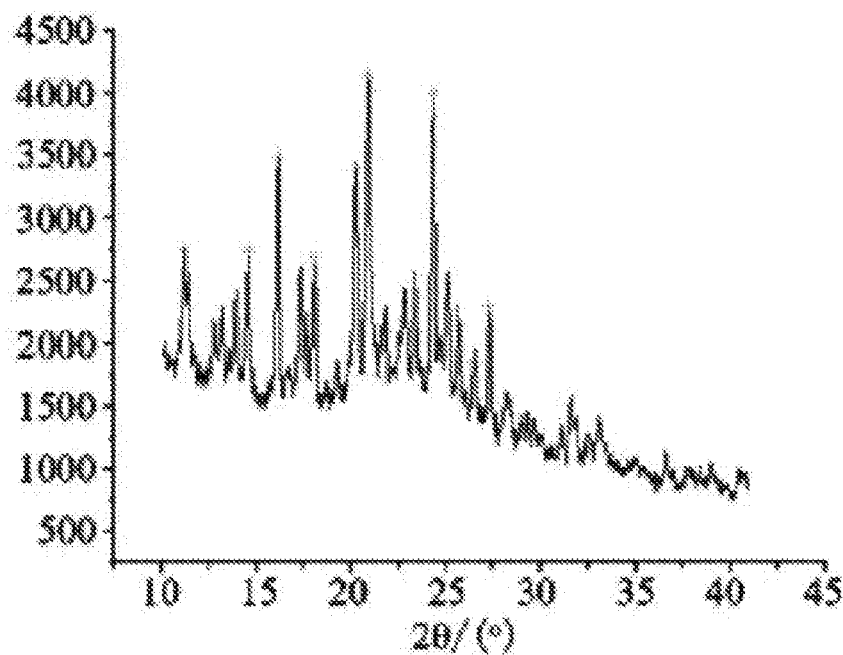
FIG. 3 provides the X-ray powder diffraction pattern of crystallized Cefathiamidine obtained in acetonitrile as the solvent reported by a literature.
Figure 4:
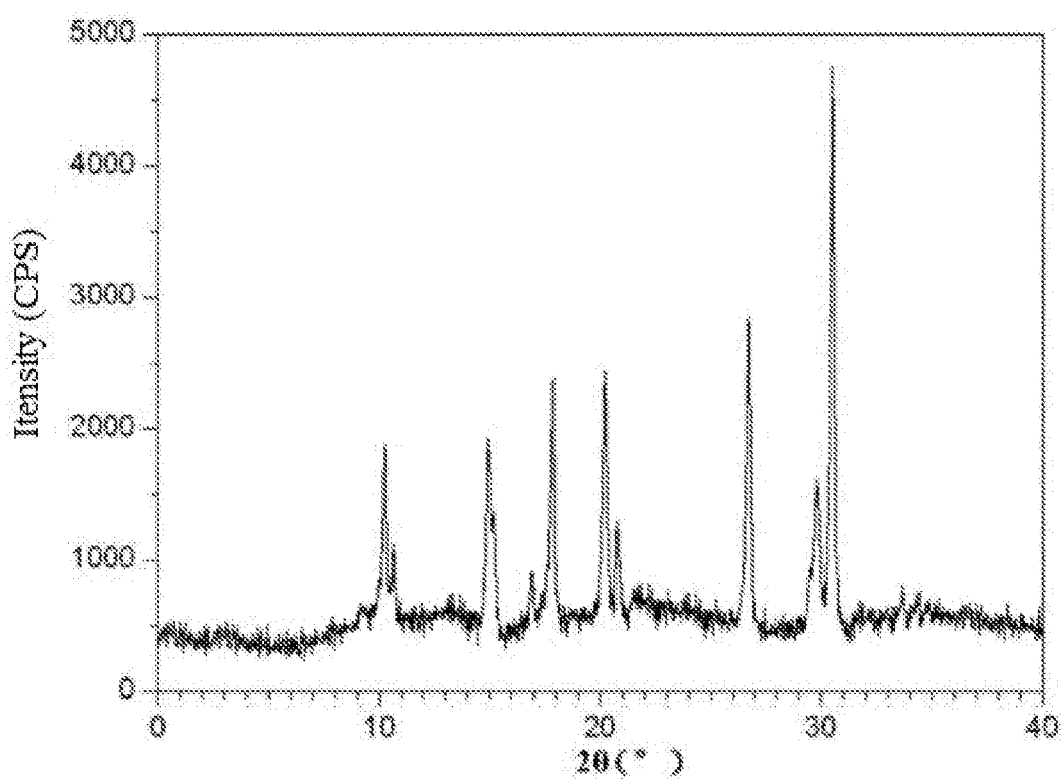
FIG. 4 provides the X-ray powder diffraction pattern of crystallized Cefathiamidine disclosed in CN103012434A.
Figure 5:
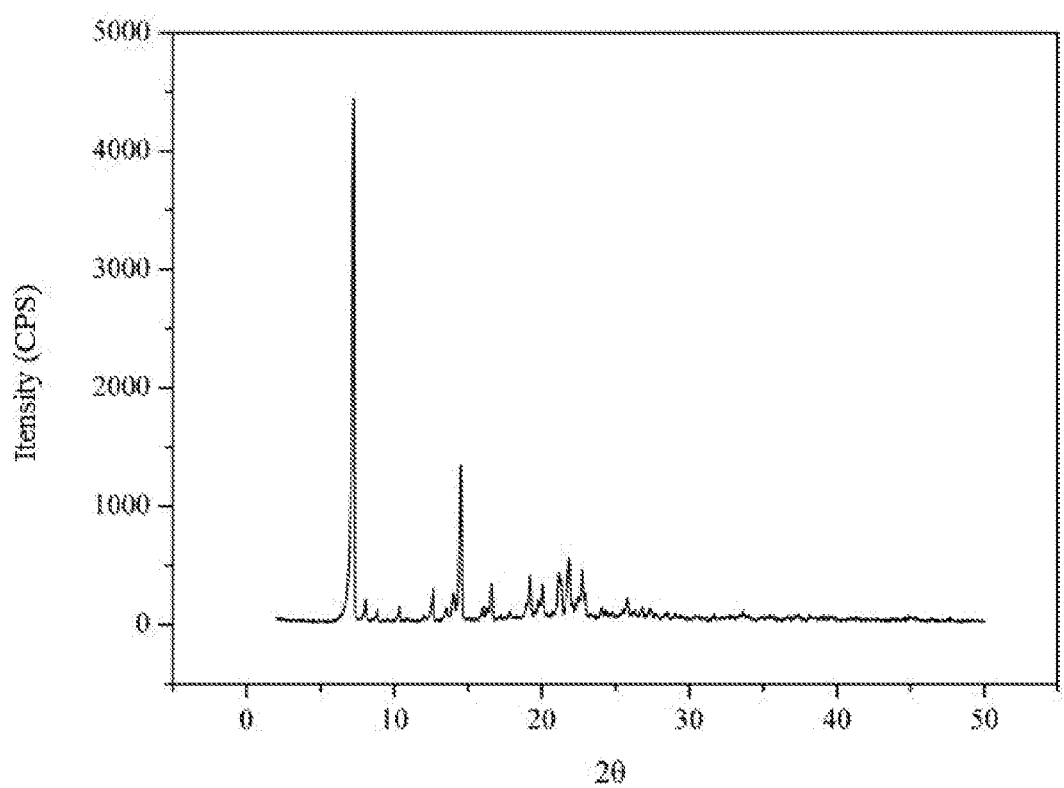
FIG. 5 provides the X-ray powder diffraction pattern of the novel crystalline form of Cefathiamidine compound of the present invention.
Figure 6:
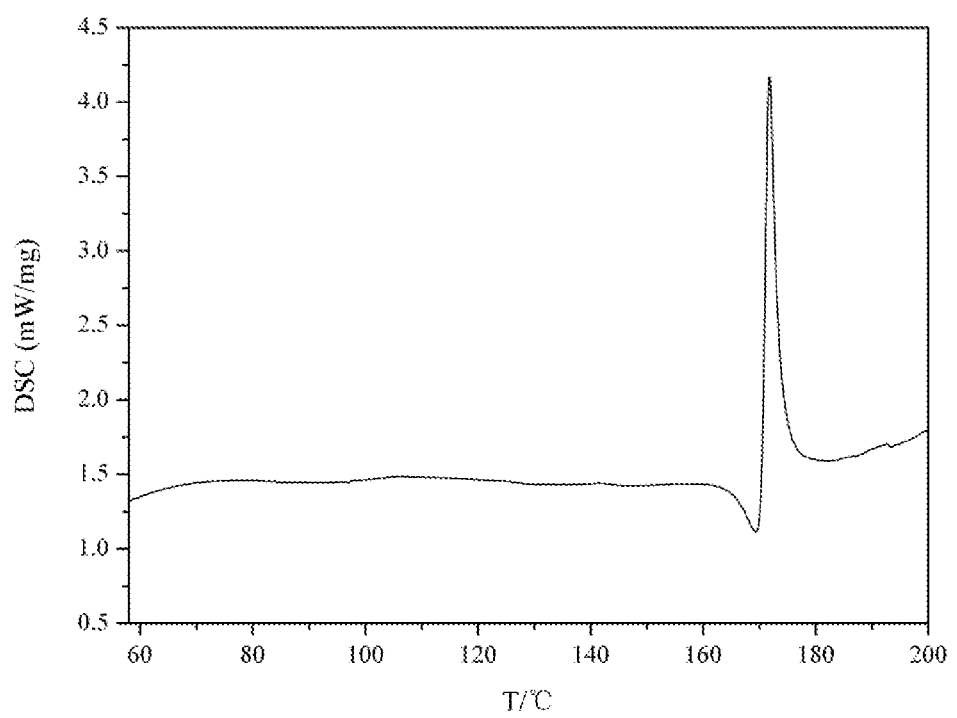
FIG. 6 provides the differential scanning calorimetry thermogram of the novel crystalline form of Cefathiamidine compound of the present invention.

5 g of solid Cefathiamidine compound with a purity of 98% was added to 100 mL of ethanol at a temperature of 45° C., until being totally dissolved to form a solution, and then 300 mL of isopropanol as a solventing-out agent was dropwise added to the solution within 3 hours; followed by cooling the solution down to 0° C. at a rate of 0.2° C./min; continuing to stir for 3 hours. The obtained solid-liquid suspension was separated, and the residue was dried at 25° C. and a vacuum of 0.08 MPa for 4 hours to provide a novel crystalline form of Cefathiamidine compound, whose PXRD pattern was shown in FIG. 5, comprising characteristic peaks (expressed in degrees 2θ) at 7.26°, 8.08°, 10.38°, 12.64°, 13.96°, 14.52°, 16.60°, 19.22°, 20.04°, 21.14°, 21.84°, and 22.74°; DSC data of the crystalline product was shown in FIG. 6, comprising a melting endothermic peak at 169.6° C. and a decomposing exothermic peak at 172.2° C. The product had a HPLC purity of 99.2% and a crystallization process mole yield of 85.5%. The novel crystalline form of Cefathiamidine compound of the present invention had a melting temperature of 169.6° C. and a thermal decomposing temperature of 172.2° C., both of which were higher than those of crystalline forms reported in any patents. Thus, the novel crystalline form of the present invention had better thermal stability, and it did not make any change within 4 months at 30° C. proved by thermal stability tests.

Example 2

15 g of solid Cefathiamidine compound with a purity of 98.3% was added to 100 mL of methanol at a temperature of 42° C., until being totally dissolved to form a solution, and then 400 mL of n-hexane as a solventing-out agent was dropwise added to the solution within 6 hours; followed by cooling the solution down to 10° C. at a rate of 0.5° C./min; continuing to stir for 3 hours. The obtained solid-liquid suspension was separated, and the residue was dried at 25° C. and a vacuum of 0.1 MPa for 8 hours to provide a novel crystalline form of Cefathiamidine compound, which had a PXRD pattern comprising characteristic peaks (expressed in degrees 2θ) at 7.24°, 8.08°, 10.38°, 12.74°, 13.86°, 14.42°, 16.70°, 19.22°, 20.04°, 21.26°, 21.84°, and 22.92°; and which also had a DSC thermogram comprising a melting endothermic peak at 169.8° C. and a decomposing exothermic peak at 172.3° C. The product had a HPLC purity of 99.4% and a crystallization process mole yield of 90.3%. The novel crystalline form of Cefathiamidine compound of the present invention had a melting temperature of 169.8° C. and a thermal decomposing temperature of 172.3° C., both of which were higher than those of crystalline forms reported in any patents. Thus, the novel crystalline form of the present invention had better thermal stability, and it did not make any change within 4 months at 30° C. proved by thermal stability tests.

Example 3

18 g of solid Cefathiamidine compound with a purity of 98.7% was added to 100 mL of water at a temperature of 30° C., until being totally dissolved to form a solution, and then 500 mL of n-butanol as a solventing-out agent was dropwise added to the solution within 6 hours; followed by cooling the solution down to 5° C. at a rate of 1° C./min; continuing to stir for 2 hours. The obtained solid-liquid suspension was separated, and the residue was dried at 30° C. and a vacuum of 0.09 MPa for 6 hours to provide a novel crystalline form of Cefathiamidine compound, which had a PXRD pattern comprising characteristic peaks (expressed in degrees 2θ) at 7.24°, 8.18°, 10.40°, 12.66°, 13.86°, 14.54°, 16.62°, 19.14°, 19.96°, 21.14°, 21.66°, and 22.76°; and which also had a DSC thermogram comprising a melting endothermic peak at 169.4° C. and a decomposing exothermic peak at 172.3° C. The product had a HPLC purity of 99.0% and a crystallization process mole yield of 89.3%. The novel crystalline form of Cefathiamidine compound of the present invention had a melting temperature of 169.4° C. and a thermal decomposing temperature of 172.3° C., both of which were higher than those of crystalline forms reported in any patents. Thus, the novel crystalline form of the present invention had better thermal stability, and it did not make any change within 4 months at 30° C. proved by thermal stability tests.

Example 4

10 g of solid Cefathiamidine compound with a purity of 98.5% was added to 100 mL of methanol at a temperature of 35° C., until being totally dissolved to form a solution, and then 400 mL of n-propanol as a solventing-out agent was dropwise added to the solution within 5 hours; followed by cooling the solution down to 0° C. at a rate of 0.6° C./min; continuing to stir for 1 hour. The obtained solid-liquid suspension was separated, and the residue was dried at 35° C. and a vacuum of 0.09 MPa for 5 hours to provide a novel crystalline form of Cefathiamidine compound, which had a PXRD pattern comprising characteristic peaks (expressed in degrees 2θ) at 7.46°, 8.28°, 10.37°, 12.75°, 13.86°, 14.48°, 16.60°, 19.22°, 20.24°, 21.34°, 21.84°, and 22.74°; and which also had a DSC thermogram comprising a melting endothermic peak at 169.7° C. and a decomposing exothermic peak at 172.0° C. The product had a HPLC purity of 99.4% and a crystallization process mole yield of 90.5%. The novel crystalline form of Cefathiamidine compound of the present invention had a melting temperature of 169.7° C. and a thermal decomposing temperature of 172.0° C., both of which were higher than those of crystalline forms reported in any patents. Thus, the novel crystalline form of the present invention had better thermal stability, and it did not make any change within 4 months at a temperature of 30° C. proved by thermal stability tests.

Example 5

20 g of solid Cefathiamidine compound with a purity of 98.7% was added to 100 mL of water at a temperature of 32° C., until being totally dissolved to form a solution, and then 350 mL of cyclohexane as a solventing-out agent was dropwise added to the solution within 3 hours; followed by cooling the solution down to 8° C. at a rate of 0.2° C./min; continuing to stir for 2 hours. The obtained solid-liquid suspension was separated, and the residue was dried at 25° C. and a vacuum of 0.08 MPa for 8 hours to provide a novel crystalline form of Cefathiamidine compound, which had a PXRD pattern comprising characteristic peaks (expressed in degrees 2θ) at 7.06°, 7.99°, 10.36°, 12.63°, 13.88°, 14.42°, 16.62°, 19.22°, 20.04°, 21.14°, 21.86°, and 22.76°; and which also had a DSC thermogram comprising a melting endothermic peak at 169.2° C. and a decomposing exothermic peak at 172.1° C. The product had a HPLC purity of 99.3% and a crystallization process mole yield of 89.6%. The novel crystalline form of Cefathiamidine compound of the present invention had a melting temperature of 169.2° C. and a thermal decomposing temperature of 172.1° C., both of which were higher than those of crystalline forms reported in any patents. Thus, the novel crystalline form of the present invention had better thermal stability, and it did not make any change within 4 months at 30° C. proved by thermal stability tests.

Example 6

12 g of solid Cefathiamidine compound with a purity of 98.5% was added to 100 mL of mixed solvents of water and ethanol at a temperature of 38° C., wherein the volume ratio of water to ethanol is 1:1, until Cefathiamidine being totally dissolved to form a solution, and then 500 mL of n-propanol as a solventing-out agent was dropwise added to the solution within 6 hours; followed by cooling the solution down to 2° C. at a rate of 0.5° C./min; continuing to stir for 1 hour. The obtained solid-liquid suspension was separated, and the residue was dried at 28° C. and a vacuum of 0.1 MPa for 5 hours to provide a novel crystalline form of Cefathiamidine compound, which had a PXRD pattern comprising characteristic peaks (expressed in degrees 2θ) at 7.14°, 8.06°, 10.18°, 12.44°, 13.76°, 14.32°, 16.64°, 19.10°, 20.16°, 21.02°, 21.64°, and 22.78°; and which also had a DSC thermogram comprising a melting endothermic peak at 169.3° C. and a decomposing exothermic peak at 171.8° C. The product had a HPLC purity of 99.3% and a crystallization process mole yield of 91.1%. The novel crystalline form of Cefathiamidine compound of the present invention had a melting temperature of 169.3° C. and a thermal decomposing temperature of 171.8° C., both of which were higher than those of crystalline forms reported in any patents. Thus, the novel crystalline form of the present invention had better thermal stability, and it did not make any change within 4 months at 30° C. proved by thermal stability tests.

Toxicity Tests and In Vitro Antibacterial Activity Tests:

The novel crystalline form of Cefathiamidine compound of the present invention was tested by toxicity tests and in vitro antibacterial activity tests (taking the crystalline form of Cefathiamidine compound obtained in Example 1 for example).

Toxicity test suggested that it had a $LD_{50}$ of $(1.10\pm0.02)$ g/kg in mice by intravenous injection and a $LD_{50}$ of $(1.30\pm0.20)$ g/kg by intraperitoneal injection, which were better than those of any prior art; and reproductive toxicity test suggested that the Cefathiamidine compound of the present invention had lower reproductive toxicity than that of any prior art, and was more suitable for clinical research.

In vitro antibacterial activity test show that it had a MIC90 of 0.24 μg/ml against *streptococcus pneumonia*, a MIC90 of 0.48 μg/ml against *streptococcus pyogenes*, a MIC90 of less than 7.8 μg/ml against another three bacterias, a MIC90 of 1.8 μg/ml against *haemophilus* influenza and a MIC90 of 1.9 μg/ml against *enterococcus*. Thus, the antibacterial activity was better than that of any prior art, and was more suitable for clinical application.

Referring to the novel crystalline form of Cefathiamidine compound and its preparation method which are disclosed and provided in the present invention, with using the present invention for reference, the person skilled in the art could make it implemented by altering materials and process parameter properly. Method and product of the present invention has already been illustrated by preferable embodiments, it will be apparent for related technicians to make changes, modifications and combinations according to the method and product provided by the present invention to achieve technology realization in the present invention, without deviating from the content, spirit and scope of the present disclosure. Especially, all of the similar replacements and modifications are obvious for those skilled in the art, which will be seen to fall within the spirit, scope and content of the present invention.

What is claimed is:

1. A crystallized Cefathiamidine, characterized in that, it has an X-ray powder diffraction pattern comprising characteristic diffraction peaks (expressed in degrees 2θ) at 7.26°±0.2°, 8.08°±0.2°, 10.38°±0.2°, 12.64°±0.2°, 13.96°±0.2°, 14.52°±0.2°, 16.60°±0.2°, 19.22°±0.2°, 20.04°±0.2°, 21.14°±0.2°, 21.84°±0.2°, and 22.74°±0.2°.

2. The crystallized Cefathiamidine according to claim 1, characterized in that, it has a differential scanning calorimetry thermogram comprising a melting endothermic peak at 169.6±1° C. and a decomposing exothermic peak at 172.2±1° C.

3. A method for preparing a crystallized Cefathiamidine, characterized in that:
dissolving Cefathiamidine compound with a purity of 98% or higher in a solvent at a temperature of 30-~45° C. to form a solution, whose concentration is controlled within 0.05-~0.2 g/mL;
adding a solventing-out agent to the solution, wherein the amount of the solventing-out agent is 3-~5 times (in volume) of that of the solvent;
cooling the solution down to 0-~10° C. at a rate of 0.2-~1° C./min;
stirring for 1-~3 hours, and separating the obtained solid-liquid suspension to provide the crystallized Cefathiamidine after drying.

4. The method according to claim 3, characterized in that, said solvent is one or more selected from the group consisting of methanol, ethanol and water.

5. The method according to claim 3, characterized in that, said solventing-out agent is selected from one or more selected from the group consisting of n-propanol, isopropanol, n-butanol, cyclohexane and n-hexane.

6. The method according to claim 3, characterized in that, said solventing-out agent is dropwise added within 3-~6 hours.

7. The method according to claim 3, characterized in that, the drying condition is: a temperature between 25 and ~35, a vacuum with air-pressure between 0.08 and ~0.1 MPa and a drying time between 4 and ~8 hours.

* * * * *